United States Patent [19]
Atkinson et al.

[11] 4,195,091
[45] Mar. 25, 1980

[54] APPETITE STIMULATING PYRROLO[2,1-B][3]BENZAZEPINES

[75] Inventors: Joseph G. Atkinson, Montreal; Patrice C. Belanger, Dollard des Ormeaux, both of Canada; David C. Remy, North Wales; Clarence S. Rooney, Worcester, both of Pa.

[73] Assignee: Merck & Co., Inc., Rahway, N.J.

[21] Appl. No.: 960,812

[22] Filed: Nov. 15, 1978

[51] Int. Cl.² .................. A61K 31/445; C07D 487/04
[52] U.S. Cl. .................. 424/267; 260/244.4; 260/326.5 B
[58] Field of Search ....................... 260/244.4; 424/267

[56] References Cited

U.S. PATENT DOCUMENTS

| | | | |
|---|---|---|---|
| 2,951,082 | 8/1960 | Sprague et al. | 260/328 |
| 3,014,911 | 12/1961 | Engelhardt | 546/203 |
| 3,428,677 | 2/1969 | Engelhardt et al. | 260/556 AR |
| 3,428,735 | 2/1969 | Engelhardt | 424/330 |
| 3,454,643 | 7/1969 | Cope et al. | 260/570.8 TC |
| 3,499,037 | 3/1970 | Engelhardt | 260/590 FB |
| 3,803,154 | 4/1974 | Drukker | 260/244.4 |
| 3,988,342 | 10/1976 | Prugh | 546/203 |
| 4,031,222 | 6/1977 | Remy | 424/267 |
| 4,056,536 | 11/1977 | Atkinson et al. | 260/326.5 B |
| 4,075,225 | 2/1978 | Rokach et al. | 260/326.31 |
| 4,112,112 | 9/1978 | Rooney et al. | 424/274 |

FOREIGN PATENT DOCUMENTS 2550395  5/1976  Fed. Rep. of Germany ........... 546/203

Primary Examiner—John D. Randolph
Assistant Examiner—Richard A. Schwartz
Attorney, Agent, or Firm—William H. Nicholson; Mario A. Monaco

[57] ABSTRACT (9-Carboxy-11H-pyrrolo[2,1-b][3]benzazepine-11-ylidene)piperidines useful as appetite stimulants, are prepared by hydrolysis of the corresponding ester or cyano derivatives.

7 Claims, No Drawings

APPETITE STIMULATING PYRROLO[2,1-B][3]BENZAZEPINES

BACKGROUND OF THE INVENTION

This invention is concerned with a new class of appetite stimulants—(9-carboxy-11H-pyrrolo[2,1-b] [3]benzazepin-11-ylidene) piperidines.

The compounds 3-carboxycyproheptadine and its 10,11-dihydro analog are known to have appetite stimulant properties. Also, the heterotricyclic pyrrolo[2,1-b] [3]benzazepine is known. Now with this invention there is described a series of (carboxy-pyrrolo[2,1-b] [3]benzazepine-11-ylidene) piperidines as potential appetite stimulants. However, studies of the carboxy derivatives of this series including 1-methyl-4-(9-carboxy-11H-pyrrolo [2,1-b] [3]benzazepine-11-ylidene) piperidine, 1-methyl-4-(2-carboxy-6, 11-dihydro-5H-pyrrolo[2,1-b] [3]benzazepin-11-ylidene) piperidine, 1-methyl-4-(9-carboxy-6,11-dihydro-5H-pyrrolo[2,1-b] [3]benzazepin-11-ylidene) piperidine, and 1-methyl-4-(2-carboxy-11H-pyrrolo [2,1-b] [3]benzazepin-11-ylidene) piperidine have led to the unexpected result that only the 9-carboxy derivatives of a 5,6-unsaturated analog are active. Therefore, it is an object of this invention to provide certain novel (9-carboxy-11H-pyrrolo[2,1-b] [3]benzazepine-11-ylidene) piperidines, and their pharmaceutically acceptable salts as a new class of appetite stimulants. Other objects of this invention are:

(1) to provide a novel method of stimulating appetite with the new compounds;
(2) to provide the novel pharmaceutical formulations comprising the new compounds; and
(3) to provide novel processes for preparing these new compounds.

DETAILED DESCRIPTION OF THE INVENTION

The new compounds of this invention have the structural formula:

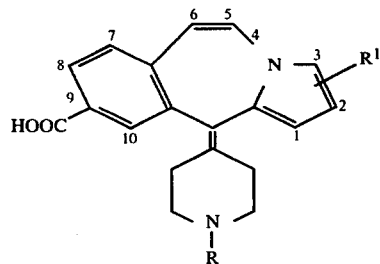

or a pharmaceutically acceptable salt or lower alkyl ester thereof, wherein:

$R^1$ is hydrogen, carboxy, lower alkyl especially $C_{1-6}$ alkyl such as methyl, propyl, or hexyl; and
R is lower alkyl especially $C_{1-6}$ alkyl or lower (cycloalkylalkyl) especially $C_{3-6}$ cycloalkyl $C_{1-3}$ alkyl such as cyclopropyl-methyl, cyclopentylethyl or the like.

A preferred embodiment of this invention is that wherein $R^1$ is in the 2-position.

Another preferred embodiment of this invention is that wherein $R^1$ is hydrogen or carboxy; and R is methyl or cyclopropylmethyl.

A more preferred embodiment of this invention is that wherein $R^1$ is hydrogen; and R is methyl.

The pharmaceutically acceptable salts mentioned above include:

(1) the acid addition salts of the amino functions obtained via treatment of the compounds with a non-toxic acid such as hydrochloric, sulfuric, phosphoric, citric, tartaric, succinic, or the like;
(2) the alkali and alkali earth metal salts and quaternary ammonium salts of the carboxylic function derived from treatment of the compounds with a non-toxic base such as sodium hydroxide, potassium hydroxide, calcium hydroxide, magnesium hydroxide, tetramethylammonium hydroxide, or the like.

The lower alkyl esters mentioned above are methyl or ethyl esters of the carboxylic acids obtained via condensation of the compounds with methanol or ethanol.

The novel process of this invention comprises the hydrolysis of a starting cyano or a carboxylic ester compound (II) to a carboxylic acid (I) as shown in scheme (a):

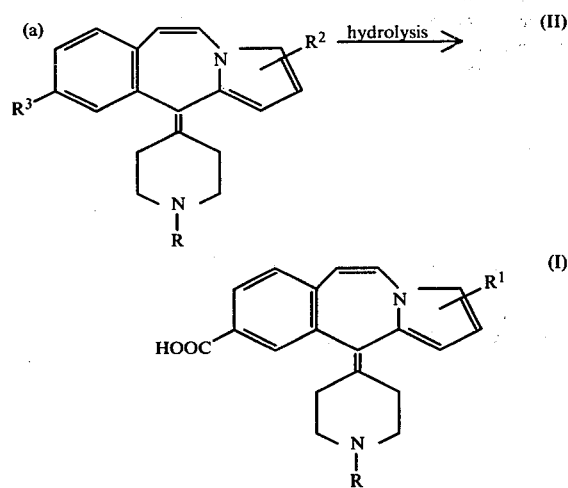

wherein:
$R^2$ is hydrogen, cyano, lower alkyl carboxylic ester especially $C_{1-4}$ alkyl carboxylic ester such as methyl, i-propyl, or t-butyl carboxylic ester, or lower alkyl;
$R^3$ is cyano or lower alkyl carboxylic ester; and
R is lower alkyl or lower (cycloalkylalkyl).

The hydrolysis is catalyzed by a strong protic base such as sodium hydroxide, or potassium hydroxide, or a strong protic acid such as hydrochloric, hydrobromic, sulfuric, trichloroacetic, or trifluoroacetic acid, preferably potassium hydroxide, in a polar solvent such as water, or a lower alkanol such as methanol, ethanol or propanol; a lower dialkyl ketone especially acetone; or mixtures thereof, preferably 80–90% aqueous ethanol, at about 25° to about 150° C., preferably at the refluxing temperature of the solvent system, until the hydrolysis is essentially complete, usually about 0.5 hr. to 6 days, preferably 3–16 hrs.

One of the starting materials of the novel process of this invention, the cyano derivative of formula (II), is prepared by treating a halo analog of formula (III):

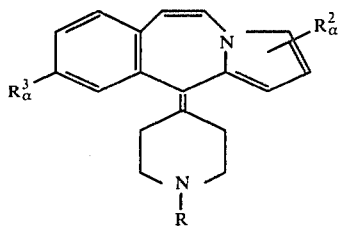

wherein:
$R_\alpha^2$ is hydrogen, halo such as iodo, bromo, or chloro, lower alkyl carboxylic ester, or lower alkyl;
$R_\alpha^3$ is halo; and
R is lower alkyl or lower (cycloalkylalkyl), with cuprous cyanide in an aprotic solvent such as N,N-dimethylformamide, dimethylsulfoxide, hexamethylphosphoramide or diethylene glycol dimethyl ether preferably N,N-dimethylformamide at about 100° to about 200° C., preferably at 150°–175° C., until the reaction is substantially complete, usually for about 3 hrs. to about 20 hrs., preferably 4–6 hrs.

The other starting carboxylic ester of formula (II), as well as the halo precursor (III) of the starting cyano compound, is prepared by the general process shown in scheme (b):

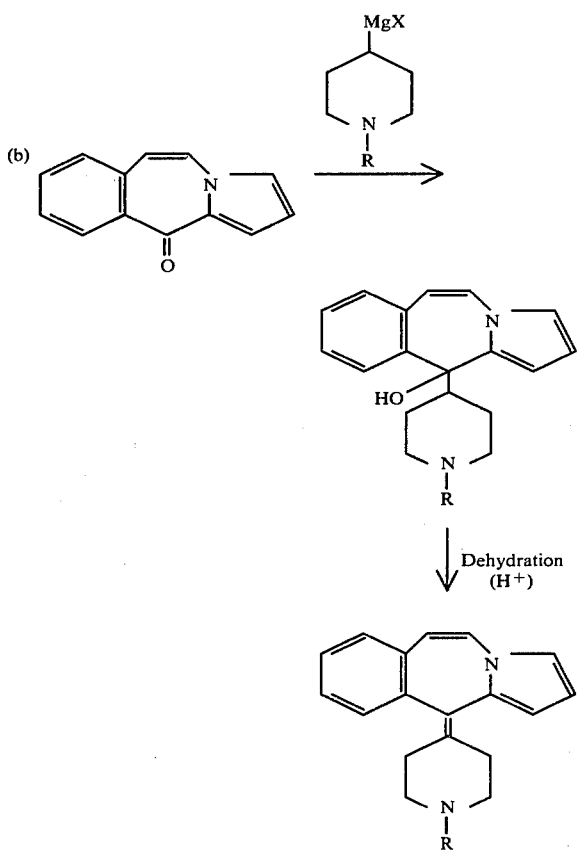

The starting ketones in scheme (b) are prepared as described in U.S. Pat. No. 4,056,536. The Grignard reaction and the subsequent dehydration also described in scheme (b) are substantially the same as those disclosed in the Patent wherein the Grignard reagent is 3-(dimethylamino)propylmagnesium chloride.

The novel appetite stimulants of structure (I) or their pharmaceutically acceptable salts can be administered to patients in need of such treatment, for example, patients suffering from Anorexia Nervosa, in any of the usual pharmaceutical forms such as powders, capsules, tablets, elixirs, and aqueous suspensions in the amount of about 1–50 mg/day, preferably about 4–15 mg/day, and preferably in divided doses taken 2 to 4 times daily.

EXAMPLE 1

1-Methyl-4-(9-carboxy-11H-pyrrolo[2,1-b][3]benzazepin-11-ylidene)piperidine

Step A: Preparation of 1-methyl-4-(9-bromo-11-hydroxy-11H-pyrrolo[2,1-b][3]benzazepin-11-yl) piperidine A suspension of 9-bromo-11H-pyrrolo[2,1-b][3]benzazepine-11-one (10.0 g., 0.036 mole) in 100 ml dry tetrahydrofuran, under a nitrogen atmosphere, is stirred in an ice bath. A solution of 1-methylpiperidine-4-magnesium chloride in tetrahydrofuran (76 ml, 0.51 M, 0.039 mole) is added dropwise. Upon completion of addition the solution is allowed to stir at room temperature for one hour after which time the solvent is removed on a film evaporator. The residue is dissolved in 300 ml benzene, the solution stirred and treated with a solution containing one gram of ammonium chloride in 10 ml $H_2O$. After one hour the mixture is filtered and the filter cake washed three times with 100 ml portions of boiling benzene. Upon evaporation of the combined filtrates in vacuo, the residue is chromatographed over a column of 400 g of silica gel packed with chloroform. A non-polar impurity is eluted with chloroform and thereafter the eluant is changed to 2%, then 5% methanol in chloroform. A second contaminant is eluted prior to the product fractions. The product fractions are combined and evaporated to give crude 1-methyl-4-(9-bromo-11-hydroxy-11H-pyrrolo[2,1-b][3]benzazepin-11-yl)piperidine (8.8 g, 65%). The crude product is used directly in the next step without further purification.

Step B: Preparation of 1-methyl-4-(9-bromo-11H-pyrrolo[2,1-b][3]benzazepin-11-ylidene) piperidene 1-Methyl-4-(9-bromo-11-hydroxy-11H-pyrrolo[2,1-b][3]benzazepin-11-yl)piperidine (8.8 g) is dissolved in 500 ml of chloroform and the solution stirred in an ice bath while dry hydrogen chloride gas is bubbled in until the solution is acidic. The flask is then stoppered and the mixture stirred at room temperature for six hours following which the mixture is carefully basified with dilute aqueous sodium carbonate. The layers are separated, the aqueous extracted twice with chloroform and the combined chloroform washed with dilute sodium bicarbonate and with water. After drying over magnesium sulfate the chloroform is removed on a film evaporator to give a dark brown oil. Trituration with acetonitrile gives slightly impure 1-methyl-4-(9-bromo-11H-pyrrolo[2,1-b][3]benzazepin-11-ylidene)piperidine (5.4 g, 64%), m.p. 138°–142° C.

Step C: Preparation of 1-methyl-4-(9-cyano-11H-pyrrolo[2,1-b][3]benzazepin-11-ylidene)piperidine 1-Methyl-4-(9-bromo-11H-pyrrolo[2,1-b][3]benzazepin-11-ylidene)piperidine (6.3 g, 0.019 mole) and cuprous cyanide (3.2 g, 0.035 mole) in 25 ml of dry dimethylformamide are refluxed under nitrogen for five hours.

The mixture is cooled to an internal temperature of 50° and treated with 60 ml each of benzene and aqueous saturated sodium cyanide solution. After stirring one hour the contents are transferred to a separatory funnel with the aid of additional benzene and water. The aqueous phase is extracted two times with benzene, once with ether and the combined benzene-ether extracts are washed successively with dilute sodium cyanide, water, dilute ammonium hydroxide, and water. Upon drying over sodium sulfate the solvents are evaporated in vacuo to give 1-methyl-4-(9-cyano-11H-pyrrolo[2,1-b][3]benzazepin-11-ylidene)piperidine as an oil (5.0 g, 87%). Trituration with acetonitrile gives a solid (3.6 g, m.p. 156°-159°). An analytical sample is obtained after one recystallization from acetonitrile, m.p. 158°-161°.

Step D: Preparation of 1-methyl-4-(9-carboxy-11H-pyrrolo[2,1-b][3]benzazepin-11-ylidene)piperidine 1-Methyl-4-(9-cyano-11H-pyrrolo[2,1-b][3]benzazepin-11-ylidene)piperidine (2.0 g, 6.6 mmole) is dissolved in 55 ml of 90% ethanol containing 1.1 g (20 mmole) potassium hydroxide and the solution is refluxed until the hydrolysis is complete (3 days). The ethanol is removed in vacuo, the residue dissolved in 120 ml of water and the aqueous solution extracted twice with ether-benzene mixtures. The aqueous phase is then carefully acidified with glacial acetic acid and the resulting suspension is concentrated to half-volume on a film evaporator. A beige solid is collected and washed with water, then with acetone to give 1.6 g, (0.005 mole, 74%) of 1-methyl-4-(9-carboxyl-11H-pyrrolo[2,1-b][3]benzazepin-11-ylidene)piperidine, m.p. 208°-215°. This solid is suspended in 20 ml absolute ethanol, cooled and treated with ethanolic hydrogen chloride (0.44 ml, 11 M). The resulting solution is evaporated at 40° in vacuo and the residue triturated with 35 ml of acetonitrile containing 1 ml of water. A black insoluble gum is filtered off and the yellow filtrate allowed to crystallize in the refrigerator. Beige crystals of 1-methyl-4-(9-carboxy-11H-pyrrolo[2,1-b][3]benzazepin-11-ylidene) piperidine hydrochloride, 1.3 g, are collected and dried at 100°/0.5 mm over phosphorous pentoxide for 12 hours. The analytically pure salt decomposes from 214° C.

EXAMPLE 2

1-Methyl-4-(2,9-dicarboxy-11H-pyrrolo[2,1-b]benzazepin-11-ylidene)piperidine

Step A: Preparation of 1-methyl-4-(2,9-dicarbomethoxy-11-hydroxy-11H-pyrrolo[2,1-b][3]benzazepin-11-yl)piperidine To a stirred solution of 12.5 g (50.0 mmole) of 2,9-dicarbomethoxy-11H-pyrrolo[2,1-b][3]benzazepine-11-one in 50 ml of anhydrous tetrahydrofuran at 70° is added dropwise an excess amount of 1-methyl-piperidin-4-yl magnesium chloride (100 mmole) in 250 ml of tetrahydrofuran. The reaction mixture is allowed to warm up to 25° C. and stirred for about 15 minutes before it is partitioned between 1.5 l of water and 0.8 l of methylene chloride. The organic layer is separated, dried over magnesium sulfate, filtered, and concentrated to a residue. It is chromatographed on a silica gel column (1.5"×17") and eluted wuth 5% (v/v) methanol in chloroform. Combination of the appropriate fractions and subsequent evaporation affords 7.1 g of 1-methyl-4-(2,9-dicarbomethoxy-11H-pyrrolo[2,1-b][3]benzazepin-11-ol)piperidine.

Step B: Preparation of 1-methyl-4-(2,9-dicarbomethoxy-11H-pyrrolo[2,1-b][3]benzazepin-11-ylidine)piperidine The hydroxy compound (100 mg) from Step A and oxalic acid (25 mg) in 2 ml of methanol is refluxed for 18 hours. The reaction solution is cooled in an ice-water bath and allowed to stand at 0°-5° C. overnight. The resulting precipitate is collected via filtration, washed with ethanol, and dried under nitrogen atmosphere to afford 97 mg of the oxalate salt of 1-methyl-4-(2,9-dicarbomethoxy-11H-pyrrolo[2,1-b][3]benzazepin-11-ylidene)piperidine, which is used directly in the next step.

Step C: Preparation of 1-methyl-4-(2,9-dicarboxy-11H-pyrrolo[2,1-b][3]benzazepin-11-ylidene)piperidine hydrochloride The ester (1.2 g) from Step B and potassium hydroxide (0.4 g) in 5 ml of ethanol is refluxed for 6 days. The reaction solution is diluted with 5 ml of water and then acidified to pH 3 with concentrated hydrochloric acid. After evaporating most of the ethanol, the mixture is extracted 5×10 ml with chloroform. The organic layers are combined and concentrated to give 1.0 g of 1-methyl-4-(2,9-dicarboxy-11H-pyrrolo[2,1-b][3]benzazepin-11-ylidene)piperidine hydrochloride.

EXAMPLES 3–11

Following the procedures substantially as described in Example 1 or Example 2, but substituting for the starting ketones and Grignard reagents used therein the substituted ketones and 1-R-piperidin-4-yl magnesium halides described in Table I in the same relative mole ratios, there are produced the new 9-carboxy derivatives of (11H-pyrrolo[2,1-b][3]benzazepin-11-ylidene)-piperidines, also described in Table I by the novel processes described previously in schemes (a) and (b).

TABLE I (I) structure shown with HOOC-substituted benzazepine fused to pyrrole bearing R$_1$, with piperidine (N-R) at the 11-ylidene position.

| Example | R | R$_1$ |
|---|---|---|
| 3 | —CH$_2$—△ | H |
| 4 | t-Bu— | H |
| 5 | —C$_2$H$_5$ | 2-COOH |
| 6 | —CH$_3$ | 2-C$_5$H$_{11}$ |
| 7 | —CH$_3$ | 3-COOH |
| 8 | t-Bu— | 2-COOH |
| 9 | —CH$_2$—△ | 2-i-C$_3$H$_7$ |
| 10 | —CH$_2$—△ | 2-COOH |
| 11 | —CH$_2$—△ | 3-COOH |

EXAMPLE 12

Pharmaceutical Compositions

A typical tablet containing 15 mg of 1-methyl-4-(9-carboxy-11H-pyrrolo[2,1-b][3]benzazepin-11-ylidene)-piperidine is prepared by mixing together with the active ingredient calcium phosphate, lactose, and starch in the amount shown in Table II. After these ingredients are thoroughly mixed, the dry mixture is blended for an additional 3 minutes. This mixture is then compressed into tablets weighing approximately 138 mg each. Similarly, tablets containing any of the new appetite stimulants of Structure (I) are prepared.

TABLE II
TABLET FORMULA

| Ingredient | Mg/Tablet |
| --- | --- |
| 1-Methyl-4-(9-carboxy-11H-pyrrolo[1,2-b][3]benzazapin-11-ylidene) piperidine | 15 |
| Calcium phosphate | 52 |
| Lactose | 60 |
| Starch | 10 |
| Magnesium stearate | 1 |

What is claimed is:

1. A compound of structural formula:

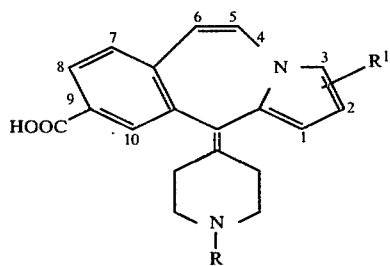
(I)

or a pharmaceutically acceptable salt or lower alkyl ester thereof, wherein:
$R^1$ is hydrogen, carboxy, lower alkyl; and
R is lower alkyl or lower(cycloalkylalkyl).

2. The compound of claim 1 wherein $R^1$ is at 2-position; $R^1$ is hydrogen or carboxy; and R is methyl or cyclopropylmethyl.

3. The compound of claim 2 wherein $R^1$ is hydrogen; and R is methyl.

4. A pharamaceutical composition for stimulating the appetite of a patient in need of such treatment comprising a pharmaceutical carrier and an effective appetite stimulating amount of a compound of structural formula:

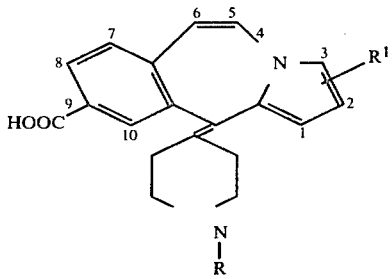

or a pharmaceutically acceptable salt thereof, wherein:
$R^1$ is hydrogen, carboxy, lower alkyl; and
R is lower alkyl or lower(cycloalkylalkyl).

5. The pharmaceutical composition of claim 4 wherein $R^1$ is hydrogen and R is methyl.

6. A method of stimulating the appetite of a patient in need of such treatment which comprises the administration to a patient an effective appetite stimulating amount of a compound of structural formula:

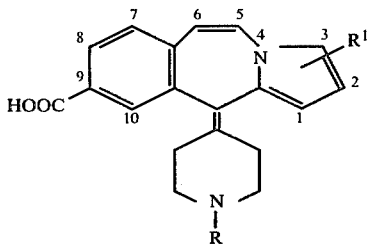

or a pharmaceutically acceptable salt thereof, wherein:
$R^1$ is hydrogen, carboxy, lower alkyl; and
R is lower alkyl or lower(cycloalkylalkyl).

7. The method of claim 6 wherein the compound is that of claim 3.

* * * * *